United States Patent [19]

Beck et al.

[11] 4,293,331
[45] Oct. 6, 1981

[54] NOVEL ACYLOXAMIDES AND PLANT GROWTH REGULANT COMPOSITIONS

[75] Inventors: Gunther Beck; Helmut Heitzer, both of Leverkusen; Klaus Lürssen, Berg.-Gladbach, all of Fed. Rep. of Germany

[73] Assignee: Bayer Aktiengesellschaft, Leverkusen, Fed. Rep. of Germany

[21] Appl. No.: 101,297

[22] Filed: Dec. 7, 1979

Related U.S. Application Data

[63] Continuation of Ser. No. 964,223, Nov. 27, 1978, abandoned.

[30] Foreign Application Priority Data

Dec. 3, 1977 [DE] Fed. Rep. of Germany ....... 2753945

[51] Int. Cl.$^3$ ..................... A01N 37/18; C07C 103/50
[52] U.S. Cl. ...................................... 71/118; 564/153
[58] Field of Search ............ 71/118, 76; 260/561 HL, 260/561 A; 564/153, 159, 160

[56] References Cited

U.S. PATENT DOCUMENTS 3,544,305  12/1970  Olin ....................................... 71/118

FOREIGN PATENT DOCUMENTS 456837  10/1967  Japan .

OTHER PUBLICATIONS

Samarai et al., Chem. Abst., vol. 73, (1970) 120566t.
Matsuura et al., Chem. Abst., vol. 70, (1969), 96703a.
Ogata et al., Chem. Abst., vol. 55, 7741c.

*Primary Examiner*—Catherine L. Mills
*Attorney, Agent, or Firm*—Sprung, Felfe, Horn, Lynch & Kramer

[57] ABSTRACT

Acyloxamide compounds of the formula

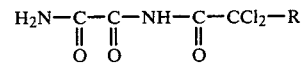

in which R is chlorine, alkyl of from 1 or 2 carbon atoms or chloroalkyl of from 1 or 2 carbon atoms and 1 to 5 chlorine atoms e.g., 2,2-dichloropropionyl-oxamide and trichloroacetyl-oxamide are outstandingly effective as plant growth regulants.

15 Claims, No Drawings

NOVEL ACYLOXAMIDES AND PLANT GROWTH REGULANT COMPOSITIONS

This is a continuation of application Ser. No. 964,223 filed Nov. 27, 1978, abandoned.

The present invention relates to certain new acyloxamides, to plant regulant compositions containing them and to methods for influencing plant growth.

It is known that (2-chloroethyl)-trimethylammonium chloride exhibits plant growth regulating properties, from U.S. Patent No. 3,156,554. However, the activity of this compound is not always completely satisfactory, especially when low amounts are used.

Furthermore, it is known that a product which is commercially available under the name "Off-Shoot-T", and is based on fatty alcohols with 6, 8, 10 and 12 carbon atoms can be employed for regulating plant growth, in particular for suppressing the growth of side shoots of tobacco (see Farm. Chem. Handbook 1975, Meister Publishing Co., Willoughby, Ohio, 1975, Pesticide Dictionary D 147). Nevertheless, in some cases, especially when low amounts are used, the activity of this product leaves something to be desired.

The present invention provides, as new compounds, acyloxamide compounds of the formula

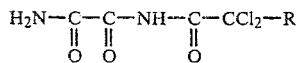  (I)

in which R is chlorine, alkyl of from 1 or 2 carbon atoms or chloroalkyl of from 1 or 2 carbon atoms and 1 to 5 chlorine atoms.

Preferably, R is chlorine, methyl, chloromethyl, dichloromethyl or trichloromethyl.

Surprisingly, the acyloxamides of the formula (I) according to the invention exhibit a considerably more powerful plant growth regulating action than (2-chloroethyl)-trimethylammonium chloride and the product "Off-Shoot-T", which are known from the state of the art and are recognized as being quite effective substances of the same type of action. The compounds according to the invention thus represent a valuable enrichment of the art.

The invention also provides a process for the preparation of an acyloxamide of the formula (I), in which an imidazolidinedione derivative of the general formula

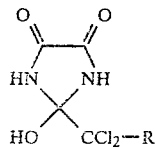  (II)

in which R has the meaning stated above,
(a) is subjected to sublimation, or
(b) is heated in a polar solvent.

If 2-hydroxy-2-trichloromethyl-imidazolidine-4,5-dione is used as the starting material, the course of the reaction, both in the case of process variant (a) and in the case of process variant (b), can be represented by the equation which follows:

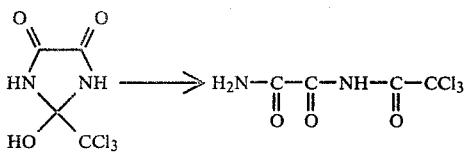

Examples which may be mentioned of compounds of the formula (II) are: 2-hydroxy-2-trichloromethyl-imidazolidine-4,5-dione, 2-hydroxy-2-(1,1-dichloroethyl)-imidazolidine-4,5-dione, 2-hydroxy-2-(1,1-dichloropropyl)-imidazolidine-4,5-dione, 2-hydroxy-2-(1,1,2-trichloroethyl)-imidazolidine-4,5-dione, 2-hydroxy-2-(1,1,2,2-tetrachloroethyl)-imidazolidine-4,5-dione and 2-hydroxy-2-(1,1,2,2,2-pentachloroethyl)-imidazolidine-4,5-dione.

The imidazolidinedione derivatives of the formula (II) are already known or can be prepared by processes which are known in principle (see DT-OS (German Published Specification) No. 2,550,157).

In carrying out process variant (a) according to the invention, the acyloxamides of the formula (I) are prepared by subjecting imidazolidinedione derivatives of the formula (II) to sublimation in vacuo. The pressure can be varied within a relatively wide range in this procedure. Thus, for example, it is possible to carry out the sublimation in a vacuum produced by a water pump, that is to say from 11 to 14 mm Hg. However, the sublimation is preferably carried out in a vacuum of the order of $10^{-1}$ to $10^{-2}$ mm Hg, such as is produced by an oil pump. The sublimation can, of course, also be carried out under considerably lower pressures. The lower limits of the pressure are imposed only by the limits of the effectiveness of vacuum pumps.

In process variant (a), the reaction temperatures can be varied within a relatively wide range. In general, the reaction is carried out at a temperature of from 100° C. to 250° C., preferably from 150° C. to 220° C.

In general, the compounds of the formula (I) are obtained in a relatively pure form during the sublimation according to process variant (a). Any impurities still contained in the product can be removed by renewed sublimation. However, in such cases it is also possible to extract the compounds of the formula (I) with the aid of suitable solvents.

In carrying out process variant (b) according to the invention, the acyloxamides of the formula (I) are prepared by heating imidazolidinedione derivatives of the formula (II) in polar solvents, usually for 5 to 50 hours. Possible polar solvents for this procedure are all the conventional inert, polar organic solvents, especially nitriles of lower aliphatic carboxylic acids (such as acetonitrile and propionitrile) and cyclic ethers (such as dioxan or tetrahydrofuran).

The reaction temperatures in process variant (b) can be varied within a relatively wide range. In general, the reaction is carried out at a temperature of from 50° C. to 150° C., preferably from 70° C. to 120° C.

In carrying out process variant (b), in general 2 to 20 ml of polar solvent are employed per gram of imidazolidinedione derivative of the formula (II). In general, the compound of the formula (I) is isolated by distilling off the solvent, after the reaction has ended, and if appropriate recrystallising the residue. If the product obtained still contains unreacted imidazolidinedione derivative of the formula (II), in addition to the acyloxamide of the formula (I), the compound of the formula (I) can be extracted from the impurities with a boiling hot cyclic hydrocarbon, such as cyclohexane, benzene or toluene. The unreacted imidazolidinedione derivative of the formula (II) remains behind as a virtually insoluble substance.

Examples which may be mentioned of the acyloxamides according to the invention are: trichloroacetyl-oxamide, 2,2-dichloropropionyl-oxamide, 2,2,3-trichloropropionyloxamide, 2,2,3,3-tetrachloropropionyl-oxamide and 2,2,3,3,3-pentachloropropionyl-oxamide.

The compounds according to the present invention engage in the metabolism of plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of the growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging.

In the case of many crop plants, inhibition of the vegatative growth permits denser planting of the crop, so that a greater yield per area of ground can be achieved.

A further mechanism of increasing the yield by means of growth inhibitors is based on the fact that the nutrients benefit blossoming and fruit formation to a greater extent, whilst vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favourably to influence the production or the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit—for example in the case of table fruit—in the sense of a chemical thinning out, up to a certain degree. Growth regulators can also be used to reduce the force required to detach the fruit from crop plants to harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators it is also possible to influence the latent period of seeds or buds of plants, that is to say the endogenic annula rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm moist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperatures and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of organic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides and herbicides, and also as a mixture with fertilisers and other growth regulators.

The active compounds can be used as such, as their formulations or as the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomising, scattering, dusting, foaming and gassing. Furthermore, it is possible to use the active compounds in accordance with the ultra-low volume process, to spread the active compound preparation or the active compound itself on plants or parts of plants or to inject the active compound preparation or the active compound itself into the soil. It is also possible to treat the seeds of plants.

The active compound concentrations can be varied within a substantial range. In general 0.01 to 50 kg, preferably 0.05 to 10 kg, of active compound are employed per hectare of soil surface.

The compounds according to the invention not only are suitable for regulating plant growth, but in addition also possess a herbicidal activity.

The present invention also provides plant-growth-regulating compositions containing as active ingredient a compound of the present invention in admixture with a solid or liquefied gaseous diluent or carrier or in admixture with a liquid diluent or carrier containing a surface-active agent.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The examples which follow show the activity of the compounds according to the invention as growth regulators, without excluding the possibility of further applications as growth regulators.

In the examples which follow, the compounds indicated below were used as comparison substances:

A = Off-Shoot-T (a plant growth regulator based on fatty alcohols with 6, 8, 10 and 12 carbon atoms).

B = Cl—$CH_2$—$CH_2$—$N^{\oplus}(CH_3)_3 Cl^{\ominus}$ (2-chloroethyl-trimethylammonium chloride).

In these biotest Examples, the active compounds according to this invention are each identified by the number of the corresponding preparative Example, given later in this text.

EXAMPLE A

Inhibition of growth of side shoots of tobacco

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Tobacco plants were grown in a greenhouse until the 7th foliage leaf had unfolded. In this stage, the apical vegetative tips of the plants were removed and the plants were sprayed with the formulations of active compound until dripping wet. After 3 weeks, the side shoots of the plants were broken off and weighed. The weight of the side shoots of the treated plants was compared with that of the untreated control plants.

In this test, the active compound 1 caused substantially better inhibition of the growth of side shoots than substance A, known from the prior art.

EXAMPLE B

Inhibition of growth of soya beans

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Soya bean plants were grown in a greenhouse until the first secondary leaf had unfolded completely. In this stage, the plants were sprayed with the preparations of active compound until dripping wet. After 3 weeks, the additional growth of the treated plants was compared with the additional growth of the untreated control plants.

In this test, active compounds 1 and 2 each caused a substantially greater inhibition of growth than substance B, known from the prior art.

EXAMPLE C

Inhibition of growth of cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Cotton plants were grown in a greenhouse until the 5th foliage leaf had unfolded completely. In this stage, the plants were sprayed with the preparations of active compound until dripping wet. After 3 weeks, the additional growth of the treated plants was compared with the additional growth of the untreated control plants.

In this test, active compound 2 caused a strong inhibition of growth.

EXAMPLE D

Inhibition of growth of wheat

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Wheat plants were grown to the 2-leaf stage in a greenhouse. In this stage, the plants were sprayed with the preparations of active compound until dripping wet. After 3 weeks, the additional growth of the treated plants was compared with the additional growth of the untreated control plants.

In this test, active compounds 1 and 2 each caused a substantially greater inhibition of growth than substance B, known from the prior art.

EXAMPLE E

Inhibition of growth of barley

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Barley plants were grown to the 2-leaf stage in a greenhouse. In this stage, the plants were sprayed with the preparations of active compound until dripping wet. After 3 weeks, the additional growth of the treated plants was compared with the additional growth of the untreated control plants.

In this test, active compounds 1 and 2 each caused a substantially greater inhibition of growth than substance B, known from the prior art.

EXAMPLE F

Inhibition of growth of grass (*Festuca pratensis*)

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Grass was grown in plastic pots of size 7 cm × 7 cm and when it had grown to a height of about 5 cm was sprayed with the preparations of active compound until dripping wet. After 3 weeks, the additional growth of the treated plants was compared with the additional growth of the untreated control plants.

In this test, active compounds 1 and 2 each caused a substantially greater inhibition of growth than substance B, known from the prior art.

PREPARATIVE EXAMPLES

Example 1

Variant (a):

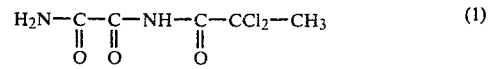

10 g of 2-hydroxy-2-(1,1-dichloroethyl)-imidazolidine-4,5-dione were heated to 180°–200° C. in a sublimation apparatus under a pressure of about 0.1 mm Hg.

After 2-3 hours, virtually all the substance had sublimed. This procedure gave 9 g (90% of theory) of 2,2-dichloropropionyloxamide, which, after recrystallisation from anhydrous cyclohexane, was obtained in the form of long thin needles and had a melting point of 110° C.

Analysis: ($C_5H_6Cl_2N_2O_3$). Calculated: 28.17%; 2.82% H; 33.33% Cl; 13.15% N; 22.54% O. Found: 28.1% C; 2.9% H; 33.6% Cl; 13.1% N; 21.9% O.

The elementary composition $C_5H_6Cl_2N_2O_3$ was also confirmed by the mass spectrum.

The most important IR bands (in $cm^{-1}$) were (KBr tablet): 3390, 3335, 3220, 1783, 1713, 1700, 1433, 1420, 1400, 1140, 1100, 1065, 782, 750, 717, 645 and 606.

Variant (b):

1,340 g of 2-hydroxy-2-(1,1-dichloroethyl)-imidazolidine-4,5-dione were stirred in 3 liters of acetonitrile under reflux (about 81° C.) for about 20 hours. After cooling the mixture to 20° C., the 12 g of oxamide formed by hydrolysis were filtered off and the filtrate was concentrated to dryness on a rotary evaporator under a water pump vacuum. The residue was kept in a vacuum drying cabinet at 70° C./0.1 mm Hg for several hours, during which a few grams of 2,2-dichloropropionic acid formed by hydrolysis sublimed out. 1,240 g of 2,2-dichloropropionyl-oxamide, corresponding to 92.5% of theory, were obtained as the residue. The properties of the substance were identical to those of the produce prepared according to variant (a).

Example 2

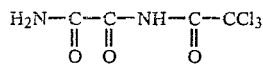
(2)

Variant (a):

10 g of 2-hydroxy-2-trichloromethyl-imidazolidine-4,5-dione were sublimed under a pressure of 0.05 mm Hg and at temperatures between 200° and 220° C. This procedure gave 8 g (80% of theory) of trichloroacetyl-oxamide, which, after recrystallisation from cyclohexane, had a melting point of 101° C. The elementary composition $C_4H_3Cl_3N_2O_3$ was confirmed by the mass spectrum.

The most important IR bands (in $cm^{-1}$) were (KBr tablet): 3418, 3385, 3335, 3250, 1795, 1741, 1697, 1515, 1490, 1390, 1350, 1150, 1090, 838, 810, 660 and 590.

Variant (b):

20 g of 2-hydroxy-2-trichloromethylimidazolidine-4,5-dione were stirred with 300 ml of acetonitrile under reflux for about 10 hours. The reaction mixture was then concentrated to dryness on a rotary evaporator under a water pump vacuum.

The IR spectrum of the residue showed that approximately one third of the mixture consisted of trichloroacetyloxamide. This compound was isolated in the pure form by extracting the product with boiling, anhydrous cyclohexane, from which the compound crystallised out on cooling. The properties of the substance were identical to those of the product prepared according to variant (a).

It will be understood that the specification and examples are illustrative but not limitative of the present invention and that other embodiments within the spirit and scope of the invention will suggest themselves to those skilled in the art.

What is claimed is:

1. Acyloxamide compound of the formula

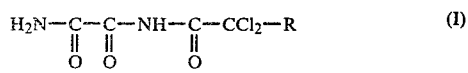
(I)

in which R is chlorine, alkyl of from 1 or 2 carbon atoms or chloroalkyl of from 1 or 2 carbon atoms and 1 to 5 chlorine atoms.

2. Acyloxamide compound as claimed in claim 1 wherein R is chlorine.

3. Acyloxamide compound as claimed in claim 1 wherein R is methyl.

4. Acyloxamide compound as claimed in claim 1 wherein R is chloromethyl.

5. Acyloxamide compound as claimed in claim 1 wherein R is dichloromethyl.

6. Acyloxamide compound as claimed in claim 1 wherein R is trichloromethyl.

7. Acyloxamide compound as claimed in claim 1 designated 2,2-dichloropropionyl-oxamide.

8. Acyloxamide compound as claimed in claim 1 designated trichloroacetyl-oxamide.

9. Plant growth regulating composition containing in growth inhibiting effective amounts, an acyloxamide compound of the formula

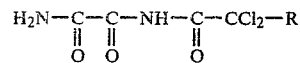

in which R is chlorine, alkyl of from 1 to 2 carbon atoms or chloroalkyl of from 1 or 2 carbon atoms and 1 to 5 chlorine atoms in admixture with a solid or liquefied gaseous diluent or carrier or in admixture with a liquid diluent or carrier containing a surface-active agent.

10. Plant growth regulating composition as claimed in claim 9 wherein said active ingredient comprises from 0.1 to 95% of the composition.

11. Method for inhibiting the growth of plants which method comprises applying to the plants or their habitat growth inhibitingly effective amounts of an acyloxamide compound of the formula

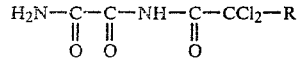

in which R is chlorine, alkyl of from 1 to 2 carbon atoms or chloroalkyl of from 1 to 2 carbon atoms and 1 to 5 chlorine atoms.

12. Method as claimed in claim 11 wherein said compound is applied to an area of plant cultivation in an amount of 0.01 to 50 kg per hectare.

13. Method as claimed in claim 12 wherein said compound is applied in an amount of 0.05 to 10 kg per hectare.

14. Method of regulating the growth of plants as claimed in claim 11 wherein said active ingredient is 2,2-dichloropropionyl-oxamide.

15. Method of regulating the growth of plants as claimed in claim 11 wherein said active ingredient is trichloroacetyloxamide.

* * * * *